United States Patent [19]

Kaufman et al.

[11] Patent Number: 5,171,755
[45] Date of Patent: Dec. 15, 1992

[54] EMULSIONS OF HIGHLY FLUORINATED ORGANIC COMPOUNDS

[75] Inventors: Robert J. Kaufman; Thomas J. Richard, both of University City, Mo.

[73] Assignee: HemaGen/PFC, San Francisco, Calif.

[21] Appl. No.: 187,854

[22] Filed: Apr. 29, 1988

[51] Int. Cl.$^5$ ............... A61K 31/02; A61K 31/03
[52] U.S. Cl. .................... 514/749; 514/759; 514/832; 514/833; 514/937; 514/975
[58] Field of Search ............. 514/759, 749, 832, 833, 514/937, 975

[56] References Cited

U.S. PATENT DOCUMENTS

| | | | |
|---|---|---|---|
| 2,055,083 | 9/1936 | Klein et al. | 167/82 |
| 3,778,381 | 12/1973 | Rosano et al. | 252/311 |
| 3,793,450 | 2/1974 | Schnell | 424/195 |
| 3,823,091 | 7/1974 | Samejima et al. | 252/312 |
| 3,911,138 | 10/1975 | Clark, Jr. | 424/352 |
| 3,914,294 | 10/1975 | Bernstein et al. | 260/519 |
| 3,942,527 | 3/1976 | Li | 128/214 R |
| 3,958,014 | 5/1976 | Watanabe et al. | 424/366 |
| 3,962,439 | 6/1976 | Yokoyama et al. | 424/248 |
| 3,975,512 | 8/1976 | Long, Jr. | 424/5 |
| 3,989,843 | 11/1976 | Chabert et al. | 424/325 |
| 3,993,581 | 11/1976 | Yokoyama et al. | 252/312 |
| 4,073,879 | 2/1978 | Long, Jr. | 424/5 |
| 4,073,943 | 2/1978 | Wretlind et al. | 424/358 |
| 4,105,798 | 8/1978 | Moore et al. | 424/352 |
| 4,110,474 | 8/1978 | Lagow et al. | 424/350 |
| 4,186,253 | 1/1980 | Yokoyama et al. | 435/240 |
| 4,252,827 | 2/1981 | Yokoyama et al. | 424/366 |
| 4,285,928 | 8/1981 | Wada et al. | 424/5 |
| 4,325,972 | 4/1982 | Geyer et al. | 424/325 |
| 4,366,169 | 12/1982 | White | 424/285 |
| 4,395,393 | 7/1983 | Schmolka | 424/78 |
| 4,397,870 | 8/1983 | Sloviter | 424/325 |
| 4,423,061 | 12/1983 | Yokoyama et al. | 424/274 |
| 4,423,077 | 12/1983 | Sloviter | 424/325 |
| 4,425,347 | 1/1984 | Yokoyama et al. | 424/256 |
| 4,443,480 | 4/1984 | Clark, Jr. | 424/352 |
| 4,446,154 | 5/1984 | Osterholm | 424/350 |
| 4,452,818 | 6/1984 | Haidt | 424/352 |
| 4,461,717 | 7/1984 | Moore | 252/312 |
| 4,486,417 | 12/1984 | Sugimoto et al. | 424/180 |
| 4,497,829 | 2/1985 | Sloviter | 514/672 |
| 4,526,969 | 7/1985 | Yokoyama et al. | 546/164 |
| 4,534,978 | 8/1985 | Yokoyama et al. | 514/429 |
| 4,542,147 | 9/1985 | Yokoyama et al. | 514/411 |
| 4,562,183 | 12/1985 | Tatlow et al. | 514/214 |
| 4,569,784 | 2/1986 | Moore | 252/315.1 |
| 4,591,599 | 5/1986 | Yokoyama et al. | 514/413 |
| 4,599,343 | 7/1986 | Yokoyama et al. | 514/299 |
| 4,657,532 | 4/1987 | Osterholm | 604/24 |
| 4,865,836 | 9/1989 | Long, Jr. | 424/5 |
| 4,866,096 | 9/1989 | Schweighardt | 514/756 |
| 4,895,876 | 1/1990 | Schweighardt et al. | 514/747 |

FOREIGN PATENT DOCUMENTS

| | | |
|---|---|---|
| 0051526 | 5/1982 | |
| 0080716 | 6/1983 | European Pat. Off. |
| 0089232 | 9/1983 | European Pat. Off. |
| 0144434 | 6/1985 | European Pat. Off. |
| 0158996 | 10/1985 | European Pat. Off. |
| 0220152 | 4/1987 | European Pat. Off. |
| 0220153 | 4/1987 | European Pat. Off. |
| 0231091 | 8/1987 | European Pat. Off. |
| 2246262 | 5/1975 | France |
| 2494992 | 6/1982 | France |
| 51-26213 | 3/1976 | Japan |
| 58-32829 | 2/1983 | Japan |
| 8403624 | 9/1984 | PCT Int'l Appl. |
| 8600810 | 2/1986 | PCT Int'l Appl. |

OTHER PUBLICATIONS

*Chem. Abstracts* 107(20):183567k, 1987, Wretlind & Ajaxon. Stabilized fat emulsion for parenteral nutrition & artificial blood.

(List continued on next page.)

*Primary Examiner*—S. J. Friedman
*Attorney, Agent, or Firm*—James F. Haley, Jr.; Emily A. Evans

[57] ABSTRACT

Improved emulsions of highly fluorinated organic compounds. The emulsions comprise a highly fluorinated organic compound, an oil, that is not substantially surface active and not significantly water soluble, and a surfactant. They are characterized by a well-defined relationship in the relative amounts of the three components.

16 Claims, 1 Drawing Sheet

OTHER PUBLICATIONS

*Chemical Abs.*, 107(18):161694x, 1987, Wretlind et al. A nutritive artificial blood emulsions having oxygen-transporting properties.

*Chem. Abs.* 85(4):25402a, 1976, Suzuki et al. Long-lasting drug micro particles.

L. C. Clark et al., "Emulsions of Perfluorinated Solvents for Intravascular Gas Transport", *Fed. Proc.*, 34, pp. 1468–1477 (1975).

R. Jeppsson, "Comparison of Pharmacological Effects of Some Local Anaesthetic Agents when using Water and Lipid Emulsion as Injection Vehicles", *Acta Pharmacol. et Toxicol.*, 36, pp. 299–311 (1975).

R. Jeppsson and S. Rössner, "The Influence of Emulsifying Agents and of Lipid Soluble Drugs on the Fractional Removal Rate of Lipid Emulsions from the Blood Stream of the Rabbit", *Acta Pharmacol. et Toxicol.*, 37, pp. 134–144 (1975).

R. Jeppsson and G. I. Schoefl, "The Ultrastructue of Lipid Particles in Emulsions Prepared with Various Emulsifiers", *Aust. J. Exp. Biol. Med. Sci.*, 52, pp. 697–702 (1974).

R. Jeppsson and B. Sjöberg, "Compatibility of Parenteral Nutrition Solutions when mixed in a Plastic Bag", *Clin. Nutr.*, 2, pp. 149–158 (1984).

R. Jeppsson et al., "Particle Size Distribution of a Fluorochemical Emulsion", in *Proceedings of the HS Symposium on Perfluorochemicals in Medicine and Biology*, Huddinge, Sweden, Apr. 28–29, 1977, V. Nováková et al., eds., pp. 108–113 (1977).

A. Wretlind, "Current Status of Intralipid and Other Fat Emulsions", in *Fat Emulsions Parenter. Nutr.*, H.-C. Meng et al., eds., American Medical Association, Chicago, Ill., pp. 109–122 (1976).

S. Ljungberg and R. Jeppsson, "Intravenous Injection of Lipid Soluble Drugs", *Acta Pharm. Suecica*, 7, pp. 435–440 (1970).

H. Ohyanagi and Y. Saitoh, "Development and Clinical Application of Perfluorochemical Artificial Blood", *Int. J. Artificial Organs*, 9, pp. 363–368 (1986).

A. Wretlind, "Development of Fat Emulsions", *J. Parenter. Enteral Nutr.*, 5, pp. 230–235 (1981).

K. Yokoyama et al., "A Perfluorochemical Emulsion as an Oxygen Carrier", Artificial Organs, 8, pp. 34–40 (1984).

D. E. Hammerschmidt and G. M. Vercelloti, "Limitation of Complement Activation by Perfluorocarbon Emulsions: Superiority of Lecithin Emulsified Preparations", *Chemical Abstracts*, vol. 109, Abstract 197120n (1988).

EMULSIONS OF HIGHLY FLUORINATED ORGANIC COMPOUNDS

TECHNICAL FIELD OF THE INVENTION

This invention relates to improved emulsions of highly fluorinated organic compounds and to processes of making and using them. More particularly, this invention relates to fluorocarbon-containing emulsions having acceptable particle size distributions both after sterilization and in the presence of serum, being safe at high doses and in total exchanges and having good shelf stability at room temperature. These emulsions comprise a highly fluorinated organic compound, an oil, that is not substantially surface active and not significantly soluble in water and a surfactant. The emulsions are characterized by a well defined relationship in the relative amounts of these three components. Such emulsions are especially useful in compositions for use as oxygen transport agents, "artificial bloods", or red blood cell substitutes, in the treatment of heart attack, stroke, and other vascular obstructions, as adjuvants to coronary balloon angioplasty and cancer radiation treatment and chemotherapy and as contrast agents for biological imaging.

BACKGROUND OF THE INVENTION

Highly fluorinated organic compounds, such as perfluorocarbon compounds ("PFC") are well known to be chemically and pharmaceutically inert. They also have the capacity of dissolving, transporting and delivering biologically and chemically significant quantities of oxygen. These properties make them potentially useful as oxygen transport agents, "artificial bloods" or red blood cell substitutes, in the treatment of heart attack, stroke and other vascular obstructions, as adjuvants to coronary angioplasty, cancer radiation treatment and chemotherapy and as contrast agents for various biological imaging modalities, such as nuclear magnetic resonance, ultrasound, x-ray and positron emission tomography.

Neat fluorocarbon liquids, however, cannot be injected into the blood stream, because their hydrophobic character makes them immiscible in the blood. As a result, they may cause vascular obstruction and death when transported into small blood vessels. Accordingly, for medical uses that require intravascular injection, such highly fluorinated organic molecules must be dispersed as physiologically acceptable, aqueous emulsions. See, e.g., L. C. Clark, Jr. et al., "Emulsions of Perfluorinated Solvents for Intravascular Gas Transport", *Fed. Proc.*, 34(6), pp. 1468–77 (1975); K. Yokoyama et a., "A Perfluorochemical Emulsion as an Oxygen Carrier", *Artif. Organs* (Ceve), 8(1), pp. 34–40 (1984); and U.S. Pat. Nos.. 4,110,474 and 4,187,252.

To date the medical usefulness of such emulsions of highly fluorinated organic compounds as "artificial bloods", red blood cell substitutes, oxygen transport agents or contrast agents for biological imaging has not been as successful as hoped. This results from the fact that none of the prior fluorocarbon-containing emulsions satisfies all of requirements of a preferred "artificial blood" or oxygen transport agent.

These requirements include:

(1) PARTICLE SIZE DISTRIBUTION (PSD) POST STERILIZATION LESS THAN 400 NM

A critical parameter for stability and safety is the PSD of the emulsion. Extensive prior art literature demonstrates that a PSD>400 nm results in excessive toxicity because the microcirculatory filters large particles leading to clogged microcirculatory vasculature and ultimately general ischemia. The particle size will also impact the rate of clearance from the circulatory system and emulsions which are not maintained in the circulatory system will not be efficacious as blood substitutes. Because terminal heat sterilization of these emulsions is necessary to eliminate the possibility of sepsis before use, emulsions which exhibit a PSD>400 nm (post sterilization) are, thus, not acceptable.

(2) Serum Stability Characterized By A PSD<400 nm After Five Days In Serum Or Ionic Solutions Of great importance to a given emulsion formulation is stability to the serum environment. A lack of serum or ionic stability results in particles that grow in vivo resulting in emboli that may clog the microvasculature and may lead to paralysis and death. In addition to the catastrophic growth that leads to death, modest in vivo particle growth results in more rapid clearance from the circulatory system and hence reduced efficacy as a red blood cell substitute or oxygen transport agent. Accordingly, emulsions which exhibit a PSD>400 nm (after 5 days in serum or ionic solutions) are not acceptable.

(3) Survival At High Doses

A major limitation to the use of an emulsion is the $LD_{50}$ or maximum safe dose. Regulatory agencies limit the use level of an emulsion based on some fraction of the $LD_{50}$. Emulsions which have a higher maximum allowable dose and, thus, can be used in higher, more effective dosages and in a broader range of clinical applications will be more broadly accepted by the medical community. An acceptable emulsion should have an $LD_{50}$ in rats of at least 16 ml/kg of the perfluorocarbon component—the active ingredient of the emulsion.

(4) Survival In Total Exchanges

Total exchange transfusions represent the most stringent test of emulsion safety and efficacy. In a total exchange, the animal's hematocrit is reduced to 3% or less, a level which would be fatal without intervention. Simultaneously, the candidate emulsion is isovolumically infused. The animal's physiologic functions, survival, general appearance and health, and intravasculature persistence are then monitored. Emulsions which lead to a high level of survival are believed to have good safety and efficacy. An acceptable emulsion should have at least a 70% survival rate in total exchanges in rats.

(5) Shelf Stability

A key criteria for the commercial utility of an emulsion is its shelf stability. Emulsions which cannot be stored for several months at either 4° C., and more preferably 25° C., will not be useful in the field. Their shelf life will be too short with respect to the time lag between manufacturing and quarantine, shipping, and usage.

In addition to these requirements, fluorocarbon-containing emulsions that are to be used as "artificial bloods" or "red blood cell substitutes" must deliver sufficient oxygen to the tissues of the body.

As is well known, blood oxygen is normally transported by hemoglobin, a highly specialized protein that on-loads oxygen in the lungs and off-loads oxygen in the tissues of the body. When atmospheric oxygen, which has an oxygen partial pressure ($pO_2$) of approximately 150 mm Hg, is breathed and is present in the alveoli of the lungs, the aterial blood $pO_2$ is about 100 mm Hg (because of the water vapor saturating the gas in the pulmonary alveoli, the bronchial circulation and other sources of arterio-venous shunting through the lungs). At this relatively low $pO_2$ all of hemoglobin's carrier sites for oxygen are almost completely saturated (97%). Thus, when the oxygen dissolved in the arterial blood plasma is in equilibrium with the hemoglobin of whole blood, 100 ml of that blood will carry about 20 ml of oxygen (20 volume percent).

When this oxygen-carrying blood moves into the capillaries where it off-loads its oxygen to the tissues, it comes into dynamic oxygen equilibrium with the oxygen present in the perivascular interstitial fluid, which on average has a $pO_2$ of 40 mm Hg. This difference in $pO_2$ level between the arterial and the venous side of the circulation permits delivery to the tissues of their normal requirement of about 5 ml of oxygen per 100 ml of whole blood (5 volume percent).

In contrast to hemoglobin which actually binds and then releases oxygen, emulsions of highly fluorinated organic compounds merely dissolve oxygen. Accordingly, the amount of oxygen delivered by a fluorocompound-containing emulsion depends on the difference between the arterial $pO_2$ and the venous $pO_2$, the solubility of oxygen in the fluorocarbon and the percentage (by volume) of the fluorocarbon in the emulsion:

Delivery of $O_2$ (volume %) =

((arterial $pO_2$ − venous $pO_2$)/760) ×

(solubility of $O_2$ in the fluorocompound) ×

(percentage (by volume) of the fluorocompound in the emulsion).

For use as an "artificial blood" or red blood cell substitute, a fluorocompound-containing emulsion should deliver at least as much oxygen as whole blood—5% by volume. At the 100% $O_2$ breathing mixture used for up to 12 hours in critical care situations, such an emulsion should, thus, contain at least about 20% by volume of the fluorocompound. E.g. (using the equation above):

desired $O_2$ delivery = 5% (by volume)

arterial $pO_2$ = 600 mm Hg (100% $O_2$)* venous $pO_2$ = 40 mm Hg solubility of $O_2$ in fluorocompound = 33% (by volume)**

percentage (by volume) of fluorocarbon required = $x$

*The approximate conventionally assumed arterial $pO_2$ of a healthy 20 year old at 100% $O_2$.
**At 37° C., most perfluorocarbon-containing compounds have similar Bunsen oxygen solubility coefficients. These range between about 0.32 to 0.35, i.e., the solubility of $O_2$ in them is between about 32 to 35% (by volume).

$$x = \frac{0.05}{\frac{(600-40)}{760}(0.33)} = 20.5\%$$

At the 40% to 80% $O_2$ breathing mixture tolerated for longer times than 12 hours in hospital settings, such emulsion should contain from about 25% to about 60% by volume of the fluorocarbon, and most preferably from 30% to 55% by volume.

It is clear from the foregoing that without relatively high PFC contents, perfluorocarbon emulsions will not be capable of delivering the quantities of oxygen that are available from whole blood. Compounding the oxygen delivery shortcomings of low % (by volume) PFC emulsions are two additional factors critical to the medical use of perfluorocarbon emulsions. The first is the need for high oxygen delivery per unit volume of fluid administered. There is a limit to the volume of fluid that can be delivered to a patient, especially if the heart or kidneys are suspected to be compromised. The second additional shortcoming of low % (by volume) PFC emulsions is that in high volume transfusions it is usually necessary to mix the infused emulsion with other solutions needed to support the ionic and oncotic needs of the patient. Therefore, dilution of low % PFC emulsions with "annex" solutions containing salts and suitable plasma expanders serves to dilute the already low oxygen delivery capacity of these formulations.

Illustrative of the deficiencies of prior fluorocarbon-containing emulsions is "Fluosol DA 20%", the only fluorocarbon emulsion to reach clinical testing as an "artificial blood". It is an about 10% (by volume) emulsion of two fluorocarbons—perfluorodecalin and perfluorotripropylamine—in a mixture of two surfactants—egg yolk phospholipid and Pluronic F-68. It is not stable in the liquid state and must be stored frozen (Yokoyama et al., supra). Furthermore, the required presence of the perfluorotripropylamine in this emulsion, to help "stabilize" it, virtually eliminates the emulsion's medical usefulness (as an artificial blood or oxygen transport agent) because the half-life of the perfluorotripropylamine in the liver and the other body tissues is longer than desirable (see, e.g., K. Yokoyama et al., supra). Finally, because this emulsion contains only about 10% fluorocarbon by volume, it is much less therapeutically effective as an "artificial blood" than desired because of its low oxygen delivery capacity—about 2.4% $O_2$ at 100% inspired oxygen (see, e.g., "Fluosol-DA As A Red Cell Substitute In Acute Anemia", *N. E. Jour. Med*, 314, pp. 1653–66 (1986)). This is substantially less than the 5 volume % oxygen which must be delivered to sustain healthy physiologic function.

Also illustrative of these deficiencies are the three fluorocarbon emulsions referred to in Jeppsson et al., "Particle Size Distribution Of A Fluorochemical Emulsion", in HS Symposium Research on Perfluorochemicals in Medicine and Biology, Huddinge, Sweden, Apr. 28–29, 1977, Karolinska Institute Research Center, Proceedings, Novakova, et al., ed., pp. 108–113 (1978). These emulsions contain about 15% (by volume) fluorocarbon—too little to be useful as an "artificial blood" or "red blood cell substitute"—a use, in fact, never even suggested by Jeppsson.

One attempt to remedy the problems of these prior art fluorocarbon-containing emulsions is described in Shaw-Clark European patent application 231,091. The emulsions of that application are characterized by high fluorocarbon contents and good stability at room temperature and after sterilization. They comprise an oil that is not substantially, surface active and not significantly soluble in water, a surfactant and a highly fluorinated organic compound. Although a vast improvement over prior emulsions, the genus of Shaw-Clark emulsions include some that do not satisfy all of the other requirements described above for emulsions preferred for use as "artificial bloods", oxygen transport agents, or contrast agents for biological imaging.

Jeppsson (supra) also refers to oil, surfactant and fluorocarbon-containing emulsions. See, e.g., Jeppsson, supra, and European patent applications 220,152 and 220,153. Jeppsson does not suggest that its emulsions permit the preferred higher concentrations of perfluorocarbons needed for "artificial bloods", oxygen transport agents or contrast agents for biological imaging. Nor does Jeppsson suggest that its emulsions satisfy the other requirements of preferred emulsions for use in these applications. In fact, the Jeppsson emulsions include many that do not satisfy all of these other requirements of the preferred emulsions described above.

SUMMARY OF THE INVENTION

This invention solves the problems referred to above. It provides for the first time emulsions of highly fluorinated organic compounds that satisfy all of the requirements of the preferred emulsions described above.

The emulsions of this invention are characterized by (1) a particle size distribution after sterilization of less than about 400 nm, and preferably less than about 300 nm; (2) a serum stability characterized by a particle size distribution of less than 400 nm, and preferably less than 300 nm, after five days in serum or ionic solutions; (3) an $LD_{50}$ in rats of at least 16 ml/kg of the fluorocarbon component of the emulsion; (4) an at least 70% survival in total exchange in rats and (5) a shelf stability of at least several months at 4° C., and preferably at 25° C.

The improved emulsions of this invention comprise at least one highly fluorinated organic compound; an oil that is not substantially surface active and not significantly soluble in water; and a surfactant. More importantly, the emulsions of this invention are characterized by specific and defined relationships in the relative amounts of those three components. The fluorocarbon component is present in the emulsion in an amount between about 10% and about 60% by volume. The amounts of the surfactant and the oil are dependent on the volume percent of fluorocarbon and are defined by the volume depicted in FIG. 1 and by the surfaces that define that volume.

This invention also includes methods of making these improved emulsions and methods and compositions of using them as oxygen transport agents, "artificial bloods" or red blood cell substitutes, and contrast agents for biological imaging, and in other medical compositions and applications known in the art.

DETAILED DESCRIPTION OF THE INVENTION

Figure 1:
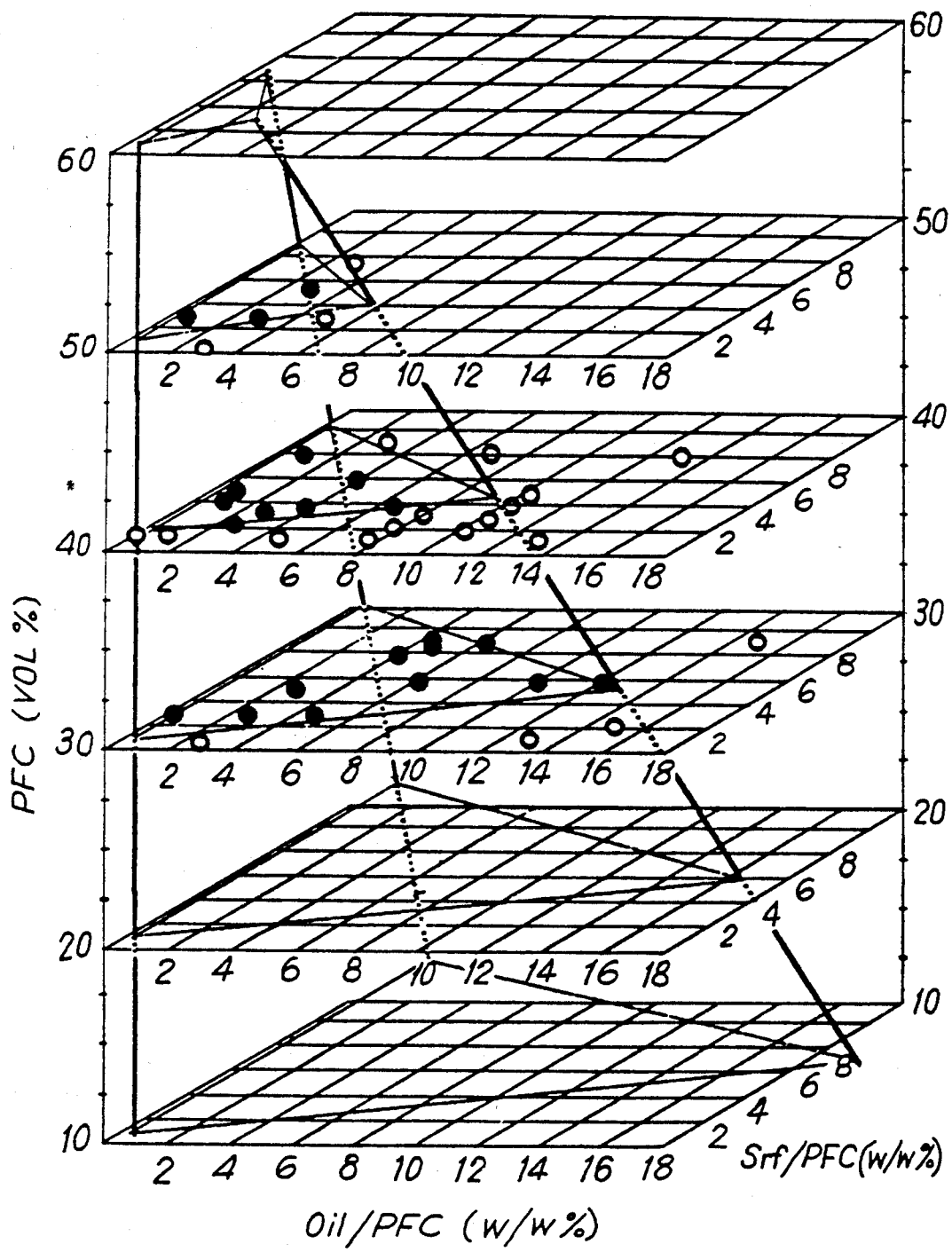
FIG. 1 is a three dimensional diagram—w/w % oil/-fluorocarbon, w/w % surfactant/fluorocarbon, and vol % fluorocarbon-containing compound—of the improved emulsions of this invention. The volume depicted in FIG. 1 and the surfaces defining it describe the improved emulsions of this invention. The filled-in circles in FIG. 1 represent emulsions of this invention that satisfy all of the requirements of the preferred emulsions described above. The open circles represent emulsions that fail in one or more of those requirements.

The emulsions of this invention comprise at least one highly fluorinated organic compound; an oil that is not substantially surface active and not significantly soluble in water; and a surfactant.

The emulsions of this invention are stable at room temperature for long periods of time—at least several months. They are stable to agitation and to mixing with various physiological additives, including, but not limited to, saline, Tyrode solution, lactated Ringer's solution, serum and serum products. They exhibit substantially no phase separation and substantially no change in particle size or droplet distribution during storage. Moreover, they permit the use of highly fluorinated organic compounds that exhibit acceptably rapid excretion times from the liver and other body tissues. And they permit the use of high concentrations of fluorocarbons, thereby producing the high oxygen delivery capacity emulsions required for use as therapeutically effective blood substitutes, oxygen transport agents and contrast agents for biological imaging. Because of their stability, they retain the above-mentioned properties even after sterilization in a conventional laboratory autoclave at 121° C. for fifteen minutes.

Among the highly fluorinated organic compounds that are useful in the emulsions and processes of this invention are those previously said to be useful as oxygen transport agents, "artificial bloods" or red cell substitutes, and contrast agents for biological imaging. These include perfluorocarbons, e.g., perfluorodecalin, perfluoroindane, perfluorotrimethylbicyclo[3.3.1]-nonane, perfluoromethyladamantane, perfluorodimethyladamantane, and perfluoro-2,2,4,4-tetramethylpentane; 9–12C perfluoroamines, e.g., perfluorotripropylamine, perfluorotributylamine, perfluoro-1-azatricyclic amines; bromo- or iodo- substituted fluorocarbons; and F-4-methyloctahydroquinolidizine and perfluoroethers. Such compounds are described, for example, in U.S. Pat. Nos. 3,962,439, 3,493,581, 4,110,474, 4,186,253, 4,187,252, 4,252,827, 4,423,077, 4,443,480, 4,534,978 and 4,542,147, European patent applications 80716 and 158,996, British patent specification 1,549,038, and German Offen. 2,650,586. Of course, it should be understood that mixtures of any of these highly fluorinated organic compounds may also be used in the emulsions and processes of this invention.

Preferably, the emulsions of this invention contain one or more of a perfluorocarbon and more preferably a perfluorocarbon selected from the group consisting of perfluorodecalin, perfluoromethyladamantane, perfluorodimethyladamantane, perfluorooctylbromide, perfluoro-4-methyloctahydroquinolidizine, perfluoro-N-methyldecahydroquinoline, F-methyl-1-oxa-decalin, perfluoro-bicyclo5.3.0]-decane, perfluorooctahydroquinolidizine, perfluoro5,6-dihydro-5-decene, and perfluoro-4,5-dihydro-4-octene. Most preferably, the perfluorocarbon is perfluorodecalin or perfluorooctylbromide. For use as a contrast agent for biological imaging, perfluorooctylbromide is the preferred highly fluorinated organic compound according to this invention.

While the highly fluorinated organic compounds, or mixture of such compounds, may comprise from about 10% to about 60% (by volume) of the emulsions, the preferred emulsions of this invention employ concentrations of at least about 20% to about 60% (by volume) of the highly fluorinated organic compound. More preferably, the emulsions of this invention comprise from about 30% to about 55% (by volume) fluorocarbon. Most preferably, the emulsions contain 40% by volume.

Among the not substantially surface active and not significantly water soluble oils that are useful in the emulsions and processes of this invention are liquid fatty oils, hydrocarbons, waxes, such as monoesters of a fatty acid and a monohydroxy alcohol, long chain ethers, diglycerides, silicone oils and nitriles. These include, for example, palmitoyl oleate, octyl nitrile, dodecyl nitrile, soybean oil, safflower oil, hexadecane, diglycerides having a $C_2$-$C_{18}$ carbon chain, and mineral oil. As with the fluoro-containing component, these oils may be used singly or in various combinations in the emulsions and processes of this inventon.

When the emulsions of this invention are to be used medically, the oil or combination of oils must, of course, be physiologically acceptable. For example, when our emulsions are to be used as "artificial bloods" or therapeutically as oxygen transport agents or contrast agents, we preferably use physiologically acceptable liquid fatty oils, such as soybean and safflower oils.

Among the surfactants useful in the emulsions of this invention are any of the known anionic, cationic, nonionic and zwitterionic surfactants. These include, for example, anionic surfactants such as alkyl or aryl sulfates, sulfonates, carboxylates or phosphates, cationic surfactants such as mono-, di-, tri-, and tetraalkyl or aryl ammonium salts, nonionic surfactants, such as alkyl or aryl compounds, whose hydrophilic moiety consists of polyoxyethylene chains, sugar molecules, polyalcohol derivatives or other hydrophilic groups that may be combinations of the above anionic or cationic groups, and whose hydrophobic moiety consists of any other polymer, such as polyisobutylene or polypropylene oxides Again, combinations of these surfactants may, of course, be used in the emulsions of this invention. In addition, mixtures of compounds, one or more of which are not surfactants, but which compounds when combined act as surfactants, may also be usefully employed as the surfactant component of the emulsions of this invention.

Again, when the emulsions of this invention are to be used in "artificial bloods" or therapeutically as oxygen transport agents or contrast agents, the surfactant, or combinations of them, must be physiologically acceptable. For example, for such uses we prefer nonionic or zwitterionic surfactants. Preferably, the surfactants used in the emulsions of this invention are one or more of the following: egg and soybean phosphatides, lecithin, and any of the series of BASF Wyandotte formulations of polyoxyethylene oxides sold under the trade name "Pluronic", especially "Pluronic F-68". Of course, many other polyethylene oxide based surfactants can be employed, but they are not typically as accessible through common channels of commerce.

In addition to the highly fluorinated organic compounds, oils, and surfactants, the emulsions of this invention contain water and may also contain, or be mixed with, other components conventionally used in "artificial bloods" or red blood cell substitutes, oxygen transport agents or contrast agents for biological imaging. These include isotonic agents, osmotic pressure controlling agents, serum extending agents and antioxidants. For example, we have successfully incorporated glycerol as a tonicity adjusting agent during the preparation of these emulsions to obtain solutions of physiologically acceptable osmolarities. The proper amounts to obtain isotonicity with respect to whole blood will be obvious to those skilled in the art. In addition, we have shown that, after preparation and heat sterilization, these emulsions may be mixed with 0.9% saline, lactated Ringer's solution, serum and serum products with no adverse affect on emulsion particle size and stability Other adjuvants can also be used in the emulsions of this invention. Among them are oncotic agents such as dextran, HES, and antioxidants.

The emulsions of this invention are characterized by a well-defined relationship in the relative amounts of the fluorocarbon, oil and surfactant components. This specific relationship or interdependence in best depicted and described by reference to FIG. 1.

In FIG. 1 the emulsions of this invention are defined as a volume on a three-dimensional plot of w/w % oil/fluorocarbon, w/w % surfactant/fluorocarbon, and % volume fluorocarbon. Emulsions falling within this volume, or on the surfaces defining it, are within the scope of this invention. Emulsions falling outside of this described volume and these surfaces are, correspondingly, not part of this invention.

Using FIG. 1, then, one of skill in the art can readily select the range of oils and the range of surfactants useful at a particular volume % fluorocarbon to prepare the emulsions of this invention. More preferably, one of skill in the art can select a particular oil and surfactant amount within that defined range for use in preparing an emulsion of this invention.

Although FIG. 1 is based on emulsions prepared with perfluorodecalin, egg yolk lecithin and safflower oil, we believe that other combinations of fluorocarbons, oils and surfactants, as described above, will display a similar interdependence of components. However, it should be understood that slightly different volumes and surfaces may define the actual interrelationship of the components of those other emulsions. It is plainly within the skill of the art based on the teachings of this application to determine those exact volumes and surfaces without undue experimentation and without departing from the scope and teachings of this invention.

In the more preferred emulsions of this invention, the fluorocarbon is perfluorodecalin, the surfactant is egg yolk lecithin, and the oil is safflower oil. In the most preferred emulsions of this invention, the perfluorodecalin is present in about 40% by volume, the lecithin present in about 2.3 w/w % lecithin/PFD and the safflower oil present in about 2.6 w/w % oil/PFD.

The emulsions of this invention may be prepared using any order of mixing the three components and water. However, we prefer to mix the oil first with a water dispersion of the surfactant. We then prepare the final emulsion by adding the fluorocarbon.

The mixing and emulsification of the components of the emulsions of this invention may be done with any of the mechanical homogenizers in commercial use, and do not require the use of extravagant equipment such as ultrasonic homogenizers, although such equipment may be used in laboratory scale production. We prefer to use an inert atmosphere to prevent degradation of the surfactant and fatty oils and to use temperatures, preferably between about 45° and 55° C. to decrease the viscosity of the material being emulsified.

In order that this invention be more fully understood, we have included the following illustrative examples. These examples do not limit the foregoing disclosure of this invention.

EXAMPLES

PROCEDURES

Preparation Of Aqueous Lecithin Dispersion

Powdered, refined, egg yolk lecithin was obtained from Kabi Vitrum and dispersed in sterile $H_2O$ under an inert atmosphere (N) using a Waring ™ Blender at high speed for 2 minutes. The blended material was transferred to a reservoir, again under an inert atmosphere, which fed a Microfluidizer ™ Model 110 homogenization apparatus. The material was cycled through the homogenizer at a flow rate of 350 ml/min, using 60 psig air pressure to drive the pump piston, for a total of 5 minutes. The temperature was maintained below 25° C. throughout. In this manner, approximately 750 g lots were prepared, at concentrations ranging from 10 to 27%. The lecithin so dispersed was collected under an inert atmosphere and stored at 4° C. All lecithin dispersions so prepared were used within one week of their preparation.

Preparation of Emulsion

The emulsifier reservoir was first loaded with the appropriate charge of sterile water, glycerol, and lecithin dispersion described above. The emulsifier was then started, and the oil was added via a syringe pump at a flow rate of from 10-30 ml/min directly into the inlet port of the homogenizer. The perfluorocarbon was then added via syringe pump at the same flow rate into the same port. The temperature was maintained at 45°-48° C. throughout, and the pH was maintained at 7.5-8.5 by controlled addition of 0.29M $NaHCO_3$ or other base. For a 250-ml batch, the material was cycled through the homogenizer at a flow rate of 300-350 ml/min for 10 minutes. Proportionately longer mean residence times were used for larger batch sizes (e.g., for a 500-ml batch, a residence time of 20 minutes was employed).

ANALYSIS

Particle Size Distribution Analysis (PSD)

Samples were analyzed according to published operating procedures on a Brookhaven BI-90 Particle Sizer. All samples were prepared in isotonic glycerol solution immediately prior to the analysis.

Serum Stability (PSD)

Samples were diluted 1:1 with a 4:1 mixture of lactated Ringer's solution and 25% human serum albumin (HSA), buffered to pH 7.2 with a phosphate buffer. Samples were incubated at 37° C. for 120 hrs. before particle size distribution analysis.

Total Exchange

Doubly cannulated rats (jugular vein/carotid artery) were isovolumically exchanged according to Goodin et al., "A Method For Evaluation Of Blood Substitutes In The Conscious Animal", *Am. Jour. Physiol.*, 245, H519-523 (1983) until the hematocrit was approximately 3%. The initial $FiO_2$ of 0.8 was reduced daily at 0.1 increments over a 4-day span, after which the animals were returned to room air. Survival was scored at 14 days.

$LD_{50}$ Analysis

The test emulsion (50 ml/kg of a 4:1 mixture of stem emulsion (40% by volume PFC) and annex (equivalent to 16 ml/kg of fluorocarbon component)) is infused at a rate of 1 ml/kg via the tail vein of 10 140-200g Sprague-Dawly rats lightly anesthetized with ether. After infusion, the animals are returned to their cage and supplied with food and water ad libitum. After 14 days the survival rate is scored. Test emulsions of other PFC volume percents would be prepared similarly to adduce 16 ml/kg of fluorocarbon component.

Shelf Stability

The test emulsions are stored in stoppered 100 ml serum bottles under a nitrogen atmosphere at 4° C. or 25° C. for at least three months. After storage, the samples are tested for particle size distribution (laser light scattering), pH, and visual quality (color, creaming, etc.).

SPECIFIC EMULSIONS

Forty-seven different emulsions were prepared in duplicate by the methods outlined in the procedures section. Each emulsion contained perfluorodecalin, safflower oil and egg yolk lecithin. The actual concentrations of the components of these emulsions are described in Table I. The emulsions were then analyzed as above The results are reported in Table 11 and plotted in FIG. 1—open circle for those that failed one or more requirements and filled-in circle for those that satisfied all requirements.

TABLE I

| Ex. No. | Lec/PFD (w/w %) | Saf/PFD (w/w %) | PFD % (v/v) |
|---|---|---|---|
| 1 | 0.66% | 2.6% | 30.0% |
| 2 | 1.15% | 13.0% | 30.0% |
| 3 | 2.08% | 17.4% | 30.0% |
| 4 | 2.60% | 0.7% | 30.0% |
| 5 | 2.60% | 2.6% | 30.0% |
| 6 | 2.60% | 5.2% | 30.0% |
| 7 | 3.99% | 10.1% | 30.0% |
| 8 | 6.08% | 6.1% | 30.0% |
| 9 | 6.08% | 13.9% | 30.0% |
| 10 | 7.99% | 4.0% | 30.0% |
| 11 | 8.68% | 5.2% | 30.0% |
| 12 | 8.68% | 17.4% | 30.0% |
| 13 | 9.03% | 4.0% | 30.0% |
| 14 | 9.03% | 8.0% | 30.0% |
| 15 | 1.30% | 0.0% | 40.0% |
| 16 | 1.30% | 1.3% | 40.0% |
| 17 | 1.30% | 4.6% | 40.0% |
| 18 | 1.30% | 7.2% | 40.0% |
| 19 | 1.30% | 13.0% | 40.0% |
| 20 | 1.95% | 2.6% | 40.0% |
| 21 | 1.95% | 5.2% | 40.0% |
| 22 | 1.95% | 7.8% | 40.0% |
| 23 | 1.95% | 10.4% | 40.0% |
| 24 | 2.60% | 2.6% | 40.0% |
| 25 | 2.93% | 2.6% | 40.0% |
| 26 | 2.93% | 5.2% | 40.0% |
| 27 | 2.93% | 7.8% | 40.0% |
| 28 | 2.93% | 10.4% | 40.0% |
| 29 | 3.91% | 1.3% | 40.0% |
| 30 | 3.91% | 3.9% | 40.0% |
| 31 | 3.91% | 6.5% | 40.0% |
| 32 | 3.91% | 10.4% | 40.0% |
| 33 | 4.60% | 1.3% | 40.0% |
| 34 | 4.60% | 13.0% | 40.0% |
| 35 | 5.20% | 0.0% | 40.0% |
| 36 | 5.99% | 3.9% | 40.0% |
| 37 | 7.81% | 0.0% | 40.0% |
| 38 | 7.81% | 1.3% | 40.0% |
| 39 | 7.81% | 7.2% | 40.0% |
| 40 | 7.81% | 13.0% | 40.0% |
| 41 | 9.11% | 2.6% | 40.0% |
| 42 | 7.81% | 2.6% | 50.0% |
| 43 | 2.60% | 2.6% | 50.0% |
| 44 | 0.66% | 2.6% | 50.0% |

TABLE I-continued

| Ex. No. | Lec/PFD (w/w %) | Saf/PFD (w/w %) | PFD % (v/v) |
|---|---|---|---|
| 45 | 2.60% | 0.7% | 50.0% |
| 46 | 2.60% | 5.2% | 50.0% |
| 47 | 5.21% | 2.6% | 50.0% |

TABLE II

| Ex.* No. | PSD (nM) | PSD (nM) Serum 120 h | Survival** (16 ml/kg PFC) | Survival Total Exchange |
|---|---|---|---|---|
| 1 | 487 | 554 | | |
| 2 | 409 | 1262 | | |
| 3 | 285 | 564 | | |
| 4 | 269 | 267 | | |
| 5 | 221 | 230 | | |
| 6 | 235 | 242 | | |
| 7 | 205 | 223 | | |
| 8 | 270 | 245 | | |
| 9 | 280 | 276 | | |
| 10 | 279 | 254 | | |
| 11 | 290 | 240 | | |
| 12 | 474 | 429 | | |
| 13 | 388 | 377 | | |
| 14 | 338 | 320 | | |
| 15 | 363 | 460 | | |
| 16 | 290 | 436 | 90% | 0% |
| 17 | 269 | 427 | | |
| 18 | 314 | 1163 | | |
| 19 | 435 | 1592 | 70% | 33% |
| 20 | 221 | 366 | | |
| 21 | 219 | — | | |
| 22 | 245 | 400 | | |
| 23 | 269 | 916 | | |
| 24 | 207 | 327 | 95% | 83% |
| 25 | 178 | 319 | | |
| 26 | 172 | | | |
| 27 | 213 | 410 | | |
| 28 | 202 | 511 | | |
| 29 | 277 | 274 | | |
| 30 | 220 | 247 | | |
| 31 | 259 | 255 | | |
| 32 | 327 | 511 | | |
| 33 | 239 | 206 | | |
| 34 | 655 | 705 | | |
| 35 | 235 | | | |
| 36 | 320 | 287 | | |
| 37 | 219 | | | |
| 38 | 379 | 306 | — | 100% |
| 39 | 513 | 466 | | |
| 40 | 595 | 838 | 0% | 67% |
| 41 | 318 | 307 | | |
| 42 | 373 | 342 | | |
| 43 | 324 | 325 | | |
| 44 | 503 | 612 | | |
| 45 | 290 | 286 | | |
| 46 | 428 | 427 | | |
| 47 | 300 | 324 | | |

*All emulsions (1–47) had a greater than three month shelf stability at room temperature as measured by particle size distribution analysis and visual inspection.
**A percent survival at 16 ml/kg PFC of less than 50% corresponds to an $LD_{50}$ of less than 16 ml/kg PFC.

While we have hereinbefore described a number of embodiments of our invention, it should be apparent that other embodiments also exist within our invention. Therefore, it should be understood that the scope of this invention is to be defined by the claims rather than by the specific embodiments which have been presented hereinbefore by way of example.

We claim:

1. A physiologically acceptable emulsion comprising a highly fluorinated organic compound, an oil that is not substantially surface active and not significantly water soluble, and a surfactant, wherein
(a) the highly fluorinated organic compound is present in an amount between about 20% and about 60% by volume and
(b) the amounts of the surfactant and oil are dependent on the volume percent of highly fluorinated organic compound and are present in amounts effective to produce emulsions characterized by (1) a particle size distribution of less than 400 nm after sterilization, (2) a serum stability characterized by a particle size distribution of less than 400 nm after 5 days in serum or ionic solutions, (3) an $LD_{50}$ in rats of at least 16 ml/kg of the highly fluorinated organic compound component of the emulsion, (4) an at least 70% survival upon total exchange in rats and (5) a shelf stability of at least several months at 4° C.

2. The emulsion according to claim 1, wherein the highly fluorinated organic compound is present in an amount between about 30% and about 55% by volume.

3. The emulsion according to claim 1, wherein the highly fluorinated organic compound is present in about 40% by volume.

4. The emulsion according to any one of claims 1, 2 or 3, wherein the highly fluorinated organic compound is selected from the group consisting of perfluorodecalin and perfluorooctylbromide.

5. The emulsion according to claim 1, wherein the oil is selected from the group consisting of safflower oil and soybean oil.

6. The emulsion according to claim 1, wherein the surfactant is egg yolk lecithin.

7. The emulsion according to claim 1, further comprising at least one compound selected from the group consisting of isotonic agents, osmotic pressure controlling agents, serum extending agents and antioxidants.

8. A red blood cell substitute comprising an amount of an emulsion according to any one of claims 1, 2, 4, 5, or 6, 7, said amount being therapeutically effective for oxygen transport and delivery in humans.

9. A composition for minimizing the adverse effects of coronary balloon angioplasty comprising a therapeutically effective amount of an emulsion according to any one of claims 1, 2, 4, 5, or 6, 7.

10. A composition for preserving organs comprising a preserving effective amount of an emulsion according to any one of claims 1, 2, 4, 5 or 6, 7.

11. A composition for treating heart attack, stroke and vascular occlusions comprising a therapeutically effective amount of an emulsion according to any one of claims 1, 2, 4, 5 or 6, 7.

12. A method for sustaining the oxygen requirements of a living organism comprising administering to the living organism in a therapeutically acceptable manner a red blood cell substitute according to claim 8.

13. A method for minimizing the adverse effects of coronary balloon angioplasty by perfusion of a composition according to claim 9 through the central lumen of the catheter.

14. A method for preserving organs by perfusion of a composition according to claim 10.

15. A method for treating heart attack, stroke and vascular occlusions comprising the step of administering to a patient in a therapeutically acceptable manner a composition according to claim 11.

16. A physiologically acceptable emulsion comprising a highly fluorinated organic compound, an oil that is not substantially surface active and not significantly water soluble, and a surfactant, wherein (a) the highly fluorinated organic compound is present in an amount between about 20% and about 60% by volume and
(b) the amounts of the surfactant and oil are dependent on the volume percent of highly fluorinated organic compound and are present in amounts effective to produce emulsions characterized by (1) a particle size distribution of less than 300 nm after sterilization, (2) a serum stability characterized by a particle size distribution of less than 300 nm after 5 days in serum or ionic solutions, (3) an $LD_{50}$ in rats of at least 16 ml/kg of the highly fluorinated organic compound component of the emulsion, (4) an at least 70% survival upon total exchange in rats and (5) a shelf stability of at least several months at 25° C.

* * * * *